US00PP07981P

United States Patent [19]

Twomey

[11] Patent Number: Plant 7,981

[45] Date of Patent: Sep. 22, 1992

[54] GRANDIFLORA ROSE PLANT NAMED TWOHAVE

[75] Inventor: Jerry Twomey, Leucadia, Calif.

[73] Assignee: DeVor Nurseries, Inc., Watsonville, Calif.

[21] Appl. No.: 640,863

[22] Filed: Jan. 11, 1991

[51] Int. Cl.[5] ..... A01H 5/00

[52] U.S. Cl. ..... Plt./21

[58] Field of Search ..... Plt./21, 22

*Primary Examiner*—Howard J. Locker

*Attorney, Agent, or Firm*—Christie, Parker & Hale

[57] ABSTRACT

A new rose plant of the grandiflora class producing red flowers.

1 Drawing Sheet

SUMMARY OF THE INVENTION

The present invention relates to a new and distinct variety of rose plant of the grandiflora rose class which was originated by my crossing as seed parent an unnamed and unpatented seedling of my creation and as pollen parent the variety known as 'Royalty' (U.S. Plant Pat. No. 4,057). The varietal denomination of this new rose is 'Twohave'.

Among the novel characteristics possessed by this new variety which distinguishes it from its parents and all other varieties of which I am aware are its attractive, brilliant scarlet red flowers borne on a plant particularly suitable for use in gardens. Flowers open well and hold their coloring as blooms age. The new variety is also characterized by its health, and disease resistance.

Asexual reproduction by budding and rooting of cuttings of the new variety as performed in Glenn County, Calif. and Kern County, Calif., shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

'Twohave' is an unusually fine grandiflora rose of bright red flower coloration. It is especially well suited for growing outdoors in gardens. The variety blooms freely under natural growing conditions and the flowers have an attractive ruffled effect at the margins.

The following is a detailed description of my new variety, with color terminology in accordance with the Royal Horticultural Society Colour Chart (R.H.S.C.C.). The terminology used in color description herein refers to plate numbers in the aforementioned color chart.

Parentage: Seedling.

*Seed parent.*—Unnamed seedling.

*Pollen parent.*—'Royalty'.

Class: Grandiflora.

The following information is from observations made of specimens grown outdoors in Watsonville, Calif.

FLOWER

Blooming habit: Continuous, profuse.

A. Bud:

(1) *Size.*—Medium; about 1.5 to 2 cm in diameter and 2.5 to 3 cm in length.

(2) *Form.*—Medium pointed.

(3) *Color.*—As sepals divide, bud color is near 46A to B.

(4) *Sepals.*—5 in number; longer than bud; simple to slightly foliaceous; hooded over bud. Color: Inside — near 146B. Outside — near 147C.

(5) *Peduncle.*—Length: 8 to 10 cm; small spines. Aspect: Straight. Strength: Erect, rigid. Color: Near 144B with tinges of near 183D.

(6) *Calyx.*—Shape: Funnel shaped; does not split. Size: Medium; 1 cm×1.25 cm long.

B. Bloom:

(1)*Size.*—Average size when fully expanded — about 9 to 10 cm; depth about 2 to 2.5 cm.

(2) *Borne.*—Clusters.

(3) *Form.*—Cupped, with beautiful ruffled effect at margins.

(4) *Petalage.*—Number of petals under normal conditions — about 19 to 21.

(5) *Color.*—After sepals fall and petals unfurl, predominant flower color viewing petals' top surface is near 46A to 45A. Color is general and substantially constant though with occasional blackening at some petal edges. Petal undersurface displays similar coloration. Ruffling at petal margins of outer petals predominant. Color at point of petal attachment is near 23B.

C. Petals:

(1) *Texture.*—Medium to thick.

(2) *Appearance.*—Inside velvety and outside satiny.

(3) *Form.*—Broad, fan shaped with some indentation or undulation at margin (slightly lobed).

(4) *Arrangement.*—Regularly arranged, imbricated.

(5) *Fragrance.*—Moderate.

(6) *Lasting Quality.*—Long lasting on plant and as cut flower; petals drop off cleanly as bloom ages.

REPRODUCTIVE ORGANS

A. Stamens:

*Number.*—Approximately 148.

*Arrangement.*—Introrse.

*Anthers.*—Size — 0.3 cm. Color — near 21C.

*Filaments.*—(Threads): Length — 0.8 to 1 cm. Color — near 46A. Pollen: Color — near 22A.

B. Pistils:

*Number.*—Approximately 102.

*Styles.*—Length — 1.5 to 2 cm. Color — near 2D with tinges of near 46D at top.

*Stigmas.*—Color — near 160A.

C. Characteristics of ovaries: Long, oblong with silvery hairs.

D. Hips:

*Fertile.*—Yes.

*Shape.*—Pear shape; 2.4 cm wide×3.1 cm long.

*Color at Maturity.*—Near 168C.

PLANT

A. Form: Upright.

B. Growth: Vigorous, upright; free branching; height attained about 127 cm at three years.

C. Foliage: Compound 3, 5 and 7 leaflets.

(1) *Size.*—Leaf size about 17 cm×14 cm.

(2) *Quantity.*—Abundant.

(3) *Color.*—Upper side — dark green. Under side — light green.

(4) *Shape.*—Oval, pointed.

(5) *Texture.*—Semi-leathery; upper side is semi-glossy, under side is matte.

(6) *Edge.*—Serrate, (denticulate).

(7) *Serration.*—Ordinary.

(8) *Leaf stem.*—Color — medium green.

(9) *Stipules.*—Hairy, adnate with glands.

(10) *Petiolule.*—About 0.2 cm.

(11) *Rachis.*—About 12 cm on 3 leaf; 14 cm on 5 leaf; 17 cm on 7 leaf.

(12) *Petioles.*—Length — 1.4 cm on 3 leaf; 3 cm on 7 leaf.

(13) *Ribs and veins.*—Ribs depressed on top; ribs and veins slightly rounded underneath. Rachis: Very few spines underneath.

(14) *Resistance to disease.*—Moderately resistant to mildew, rust and black spot.

D. Wood:

(1) *New wood.*—Color — purple/red. Bark — smooth.

(2) *Old wood.*—Color — near 183B tinged with near 144B. Bark — smooth.

E. Thorns:

(1) *Thorns.*—Quantity (main stalk) — average. On laterals from stalk — average. Form — declining slightly. Size — vary, 1 to 1.5 cm. Color — near 183C at base with tinges near 146D at tip. Position — irregular.

(2) *Prickles.*—Few to none present.

F. Winter hardiness: Needs protection in severe climates.

I claim:

1. A new and distinct variety of rose plant of the gransflora rose class, substantially as shown and described.

* * * * *

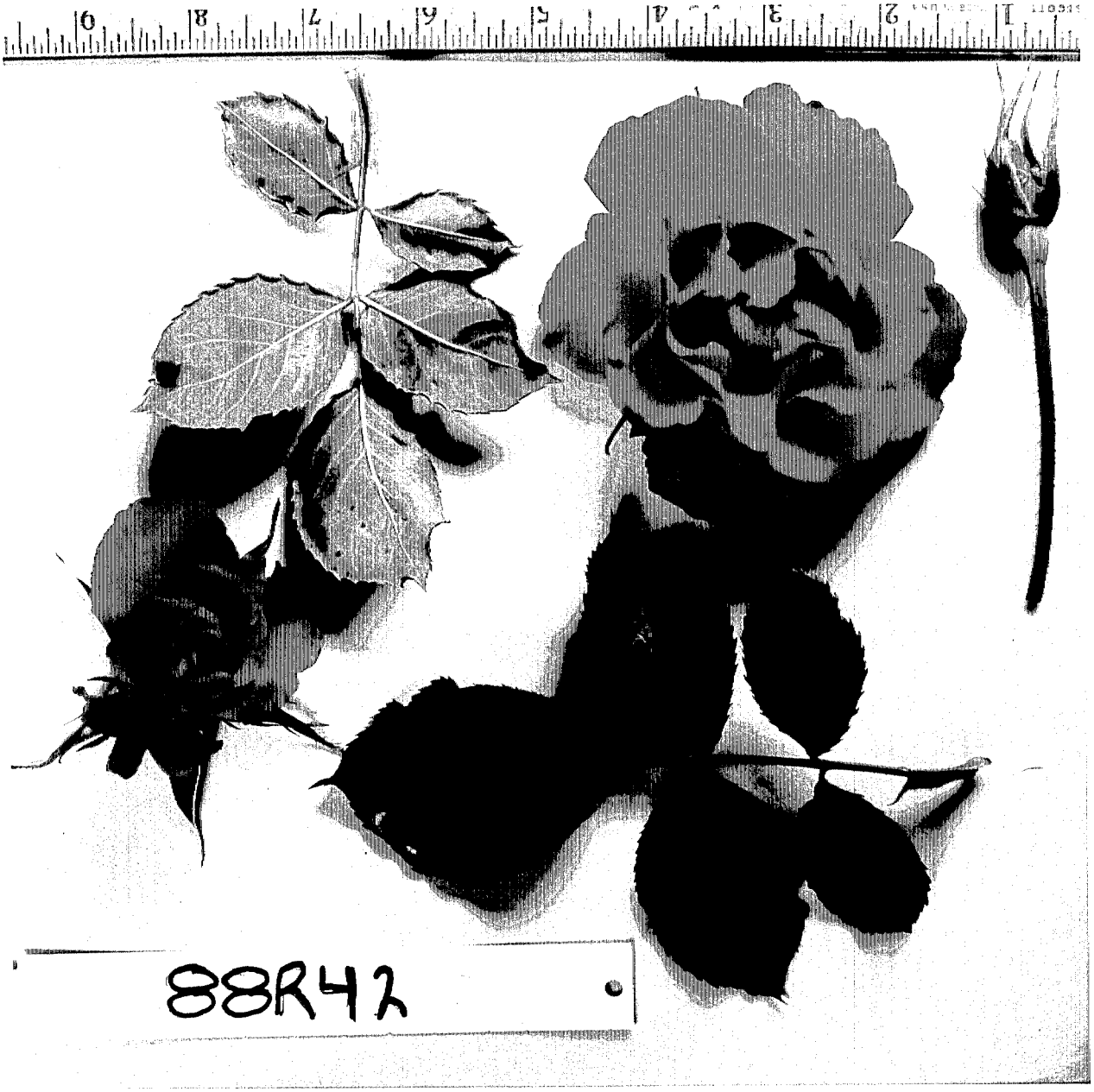
88R42

UNITED STATES PATENT AND TRADEMARK OFFICE

CERTIFICATE OF CORRECTION

PATENT NO. : Plant 7,981

DATED : September 22, 1992

INVENTOR(S) : Jerry Twomey

It is certified that error appears in the above-identified patent and that said Letters Patent is hereby corrected as shown below:

Column 4, line 27, change "gransflora" to -- grandiflora --.

Signed and Sealed this

Nineteenth Day of October, 1993

*Attest:*

*Attesting Officer*

BRUCE LEHMAN

*Commissioner of Patents and Trademarks*